United States Patent
Rodgers (10) Patent No.: US 11,260,211 B2
(45) Date of Patent: Mar. 1, 2022

(54) VARIABLE VOLUME INFUSION PORT

(71) Applicant: Primo Medical Group, Inc., Stoughton, MA (US)

(72) Inventor: Richard P. Rodgers, Hudson, MA (US)

(73) Assignee: PRIMO MEDICAL GROUP, INC., Stoughton, MA (US)

(*) Notice: Subject to any disclaimer, the term of this patent is extended or adjusted under 35 U.S.C. 154(b) by 129 days.

(21) Appl. No.: 15/905,202

(22) Filed: Feb. 26, 2018

(65) Prior Publication Data

US 2019/0262597 A1   Aug. 29, 2019

(51) Int. Cl.
*A61M 39/04* (2006.01)
*A61M 39/02* (2006.01)

(52) U.S. Cl.
CPC ..... *A61M 39/04* (2013.01); *A61M 2039/0205* (2013.01); *A61M 2039/0258* (2013.01); *A61M 2039/0276* (2013.01); *A61M 2205/0216* (2013.01)

(58) Field of Classification Search
CPC .......... A61M 39/0205; A61M 39/0208; A61M 39/04; A61M 2039/0258; A61M 2039/0276; A61M 2039/0226
See application file for complete search history.

(56) References Cited

U.S. PATENT DOCUMENTS

| | | |
|---|---|---|
| 4,360,019 A | 11/1982 | Portner et al. |
| 4,373,527 A | 2/1983 | Fischell |
| 4,832,054 A * | 5/1989 | Bark ............... A61M 39/0208 128/899 |
| 5,476,460 A | 12/1995 | Montalvo |
| 6,478,783 B1 * | 11/2002 | Moorehead ....... A61M 5/14276 604/132 |
| 7,186,236 B2 * | 3/2007 | Gibson ............ A61M 5/14276 604/93.01 |

(Continued)

FOREIGN PATENT DOCUMENTS

WO   2014205197   12/2014

OTHER PUBLICATIONS

International Search Report and Written Opinion dated May 28, 2019, issued in PCT International Patent Application No. PCT/US2019/019343, 10 pages.

(Continued)

*Primary Examiner* — Laura A Bouchelle
(74) *Attorney, Agent, or Firm* — Grossman, Tucker, Perreault & Pfleger, PLLC (57) ABSTRACT

A variable volume infusion port is provided. The infusion port may include a port body having an internal fluid reservoir, a septum, a stem to fluidly couple to a catheter lumen, and a displaceable member disposed in the internal fluid reservoir. In a first position, the displaceable member is disposed proximate the septum, providing a relatively small fluid volume within the infusion port. Insertion of an injection device through the septum causes the displaceable member to move to a second location distal from the septum, providing a relatively large fluid volume within the infusion port for the duration the injection device remains in the infusion port. The displaceable member may include a rigid member operably coupled to a biasing element or a flexible member coupled to a biasing element.

20 Claims, 6 Drawing Sheets

(56) References Cited

U.S. PATENT DOCUMENTS

| | | |
|---|---|---|
| 7,811,266 B2 | 10/2010 | Eliasen |
| 8,182,453 B2 | 5/2012 | Eliasen |
| 9,744,343 B2 | 8/2017 | Eliasen |
| 2003/0050626 A1 | 3/2003 | Gibson et al. |
| 2004/0249363 A1 | 12/2004 | Burke et al. |
| 2007/0255260 A1 | 11/2007 | Haase |
| 2012/0109080 A1* | 5/2012 | Manesis .................. A61M 5/31 |
| | | 604/288.01 |

OTHER PUBLICATIONS

Extended Search Report in related European Application No. 19756684.7, dated Oct. 19, 2021.

* cited by examiner

VARIABLE VOLUME INFUSION PORT

TECHNICAL FIELD

The present disclosure relates to medical devices, more particularly to an infusion port.

BACKGROUND

An infusion port provides care providers with a readily accessible means for delivery of intravenous fluids, such as stem cell therapies and chemotherapies. A typical infusion port includes a port body, a septum, and a port stem to which a vascular delivery catheter may be attached. Once implanted, the septum is penetrated with a needle from outside the infusion port. The port body includes a fixed internal volume and has a depth that is typically restricted by the need to use non-coring needles to limit septum damage and maximize the life of the septum. The diameter of the port body and the septum is typically dependent on the indicated use and clinical requirements. Some fixed volume internal to the port body is inherent in its design and use. In use, injected medication may be flushed from the fixed volume of the port body (and the catheter) using saline solution. The saline solution necessarily dilutes the fluids or medications remaining in the port body and catheter. In the case of expensive or difficult to procure fluids or medications, it may be desirable to avoid such dilution. Examples of such medications include chemotherapy medications and stem cell therapies.

BRIEF DESCRIPTION OF THE DRAWINGS

Features and advantages of various embodiments of the claimed subject matter will become apparent as the following Detailed Description proceeds, and upon reference to the Drawings, wherein like numerals designate like parts, and in which:

Although the following Detailed Description will proceed with reference being made to illustrative embodiments, many alternatives, modifications and variations thereof will be apparent to those skilled in the art.

DETAILED DESCRIPTION

The systems and methods described herein provide a variable volume infusion port that includes hollow body and septum that, together, form a reservoir. A displaceable member is disposed in the reservoir. In the absence of an applied force, a displaceable member remains in a first position proximate the septum to provide a reservoir having a relatively small first fluid volume. Insertion of an injection device into the reservoir applies a force that displaces the displaceable member away from the septum to provide a reservoir having relatively large second fluid volume. The second fluid volume is maintained for the duration the injection device remains in the reservoir. Withdrawing the injection device from the reservoir removes the applied force from the displaceable member causing the displaceable member to return to the first position, forcing the liquid in the reservoir into a stem that fluidly couples the reservoir to an intravenous catheter. Evacuating the liquid from the reservoir advantageously reduces or even eliminates the need for flushing the infusion port. The systems and methods described herein therefore beneficially minimize dilution caused by flushing fixed volume infusion ports with saline.

A variable volume infusion port is provided. The variable volume infusion port may include a hollow body forming a reservoir, the hollow body including a base and an open top. The variable volume infusion port may further include a septum disposed across at least a portion of the open top and a hollow stem in fluid communication with the reservoir, the hollow stem projecting at least partially from the hollow body. The variable volume infusion port may further include a displaceable member disposed in the reservoir to provide a variable volume reservoir. The displaceable member may be biased, in the absence of an insertion of an injection device into the reservoir, to a first position proximate the septum such that the reservoir contains a first fluid volume. At least a portion of the displaceable member displaceable by the insertion of the injection device into the reservoir to a second position distal from the septum such that the reservoir contains a second fluid volume that is greater than the first fluid volume.

A variable volume infusion port is provided. The variable volume infusion port may include a means for providing a reservoir in a subcutaneous infusion port and a means for varying a fluid volume of the reservoir responsive to insertion of an injection device at least partially into the reservoir such that in the absence of the injection device, the reservoir contains a first fluid volume and in the presence of the injection device, the reservoir contains a second fluid volume that is greater than the first fluid volume.

A variable volume infusion port is provided. The variable volume infusion port may include an infusion port forming an internal reservoir having a longitudinal axis and a displaceable member disposed at least partially within the internal reservoir, transverse to the longitudinal axis, the displaceable member to provide a variable fluid volume in the internal reservoir. The displaceable member may be biased, in the absence of an insertion of an injection device into the internal reservoir, to a first position along the longitudinal axis, the first position to provide a first fluid volume within the internal reservoir. The insertion of the injection device into the fluid reservoir may displace at least a portion of the displaceable member to a second position along the longitudinal axis, the second position provides a second fluid volume within the internal reservoir that is greater than the first fluid volume.

As used herein, the term "longitudinal axis" refers to an axis substantially perpendicular to the base of the fluid reservoir and substantially perpendicular to the insertion surface of the infusion port septum.

Figure 1A:
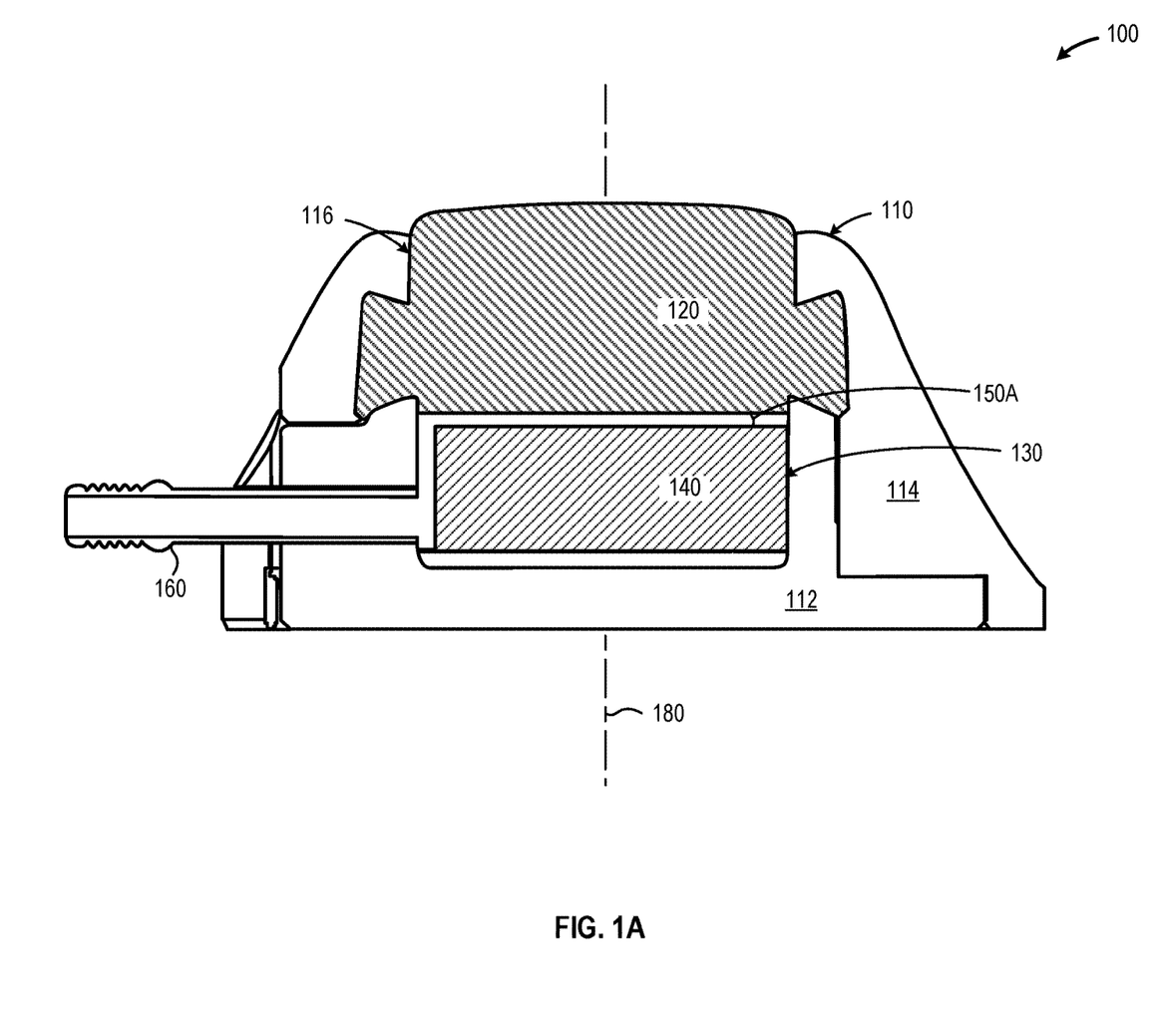
FIG. 1A is a cross-sectional elevation of a variable volume infusion port that includes a port body and septum that together form a reservoir having a defined volume, a displaceable member positioned in the reservoir is disposed in a first position proximate the septum to provide a relatively small first fluid volume in the reservoir, in accordance with at least one embodiment described herein.
Figure 1B:
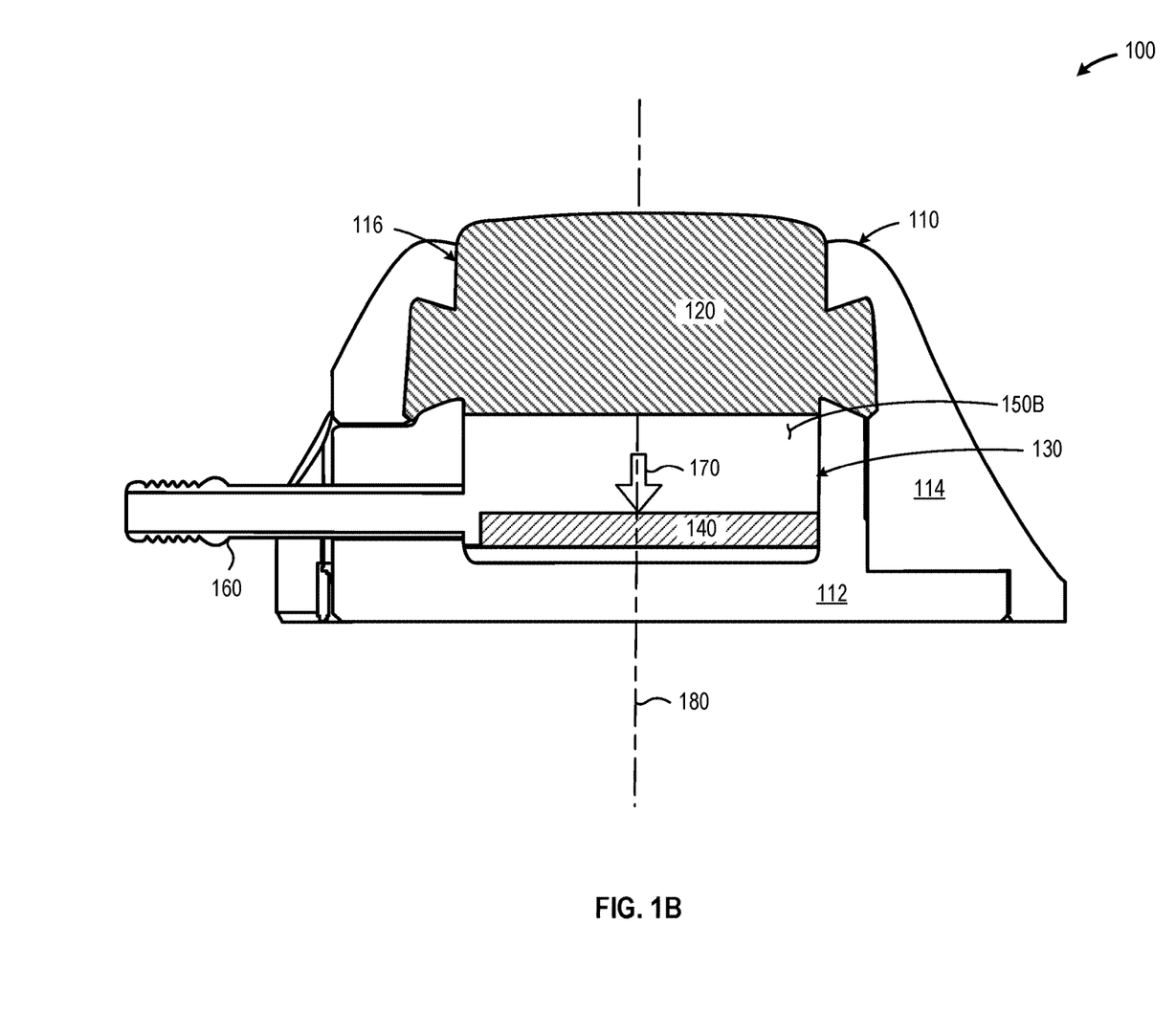
FIG. 1B is a cross-sectional elevation of the variable volume infusion port depicted in FIG. 1A with the displaceable member disposed in a second position, distal from the septum to provide a second fluid volume in the reservoir, in accordance with at least one embodiment described herein.

FIG. 1A is a cross-sectional elevation of a variable volume infusion port 100 that includes a port body 110 and septum 120 that together form a reservoir 130 having a defined volume, a displaceable member 140 positioned in the reservoir 130 is disposed in a first position proximate the septum 120 to provide a relatively small first fluid volume 150A in the reservoir 130, in accordance with at least one embodiment described herein. FIG. 1B is a cross-sectional elevation of the variable volume infusion port 100 depicted in FIG. 1A with the displaceable member 140 disposed in a second position, distal from the septum 120 to provide a second fluid volume 150B in the reservoir 130, in accordance with at least one embodiment described herein. The displaceable member 140 may be continuously, variably, displaced from the first position to the second position by applying a force 170 to the displaceable member 140. In embodiments, the force 170 may be applied to the displaceable member 140 via insertion of an injection device through the septum 120. Fluids may flow from the reservoir via a hollow stem 160 in fluid communication with the reservoir 130. In embodiments, a catheter (not depicted in FIG. 1A or 1B) may be coupled to the hollow stem 160.

The port body 110 forms an open-top, cup-shaped, reservoir 130 sealed by the septum 120. The size of the port body 110 may be selected based upon the intended use of the infusion port and/or patient needs. The port body 110 may be formed from any biocompatible material including, but not limited to: one or more biocompatible plastics, one or more biocompatible metals, one or more biocompatible ceramics, or combinations thereof.

In embodiments, such as depicted in FIGS. 1A and 1B, the port body 110 may be fabricated as a multi-piece assembly that may include a body portion 112 and a housing 114. The septum 120 may be disposed between the body portion 112 and the housing 114. An opening 116 on the surface of the housing 114 permits access to the septum 120. An injection device may be passed through the septum 120 to access and deliver fluids to the reservoir 130. The multi-piece port body 110 may be assembled using one or more techniques. In some implementations, corresponding surface features on the body portion 112 and the housing 114 may permit a "snap-fit" between the body portion 112 and the housing 114. In some implementations, surface features such as male threads and corresponding female threads may permit a threaded connection between the body portion 112 and the housing 114. In other implementations, one or more biocompatible adhesives may bond the body portion 112 to the housing 114. In other implementations, the body portion 112 and the housing 114 may be thermally bonded. In other embodiments, the port body 110 may be fabricated as a single piece, for example via injection molding.

The port body 110 may have an overall height of: about 5 millimeters (mm) or less; about 10 mm or less; about 15 mm or less; or about 20 mm or less. The port body may have a diameter of: about 15 millimeters (mm) or less; about 20 mm or less; about 30 mm or less; about 40 mm or less; or about 50 mm or less. In embodiments, the reservoir 130 may have a volume of: about 0.2 milliliters (ml) or less; about 0.5 ml or less; about 1 ml or less; about 1.5 ml or less; about 2.0 ml or less; about 3.0 ml or less; or about 5.0 ml or less. Although not depicted in FIG. 1A or 1B, the port body may include a plurality of suture holes used to affix the infusion port 100 in use.

The septum 120 seals against the body portion 112 and the housing 114. In embodiments, the septum 120 may be compressed and seal against the body portion 112 and the housing 114. In other embodiments, one or more biocompatible adhesives or sealants may be disposed about at least a portion of the septum 120 to seal the septum against the body portion 112 and housing 114. The septum 120 may be formed using one or more self-sealing, needle penetrable, biocompatible elastomer, such as silicone or polyurethane. In some embodiments, a longitudinal axis 180 may extend substantially perpendicularly from the base of the body portion 112 through the fluid reservoir 130 and substantially perpendicularly to the exposed injection surface of the septum 120.

The displaceable member 140 is disposed within the reservoir 130. In embodiments, a fluid tight seal may be formed between the displaceable member 140 and at least a portion of the inner surface of the body portion 112. The reservoir 130 may have any horizontal cross section. For example, the reservoir may have a circular, oval, or polygonal horizontal cross-section. In embodiments, the reservoir 130 may have an irregular horizontal cross section, for example a spiral shaped cross section to promote fluid flow from the reservoir via the stem 160.

As depicted in FIG. 1A, when the displaceable member 140 is disposed in the first position proximate the septum 120, a relatively smaller first fluid volume 150A forms in the reservoir 130. As depicted in FIG. 1B, when the displaceable member 140 is disposed in the second position distal from the septum 120, a relatively larger second fluid volume 150B forms in the reservoir 130. In embodiments, the first fluid volume 150A may be: about 5% or less; about 10% or less; about 20% or less; about 30% or less; or about 40% or less of the volume of the reservoir 130. The second fluid volume 150B depends on the extent to which the displaceable member 140 is displaced. In embodiments, the second fluid volume may be: about 50% or more; about 60% or more; about 70% or more; about 80% or more; or about 90% or more of the volume of the reservoir. The displaceable member 140 may include any number and/or combination of continuously displaceable systems or devices capable of movement between the first position and the second position to provide a variable fluid volume 150A-150B within the reservoir 130 upon application of a force 170 to the displaceable member 140.

The stem 160 provides an outlet from the reservoir 130 that permits the delivery of fluids to a predetermined location within the body. In a similar manner, the stem 160 may permit the extraction of fluids from a predetermined location within the body via aspiration. Delivery of fluids to the body is accomplished by transporting the fluid through a catheter attached to the stem 160. The stem 160 may therefore be configured to accept the lumen of a catheter. The distal end of the stem may include one or more features, such as the barbs illustrated in FIGS. 1A and 1B, to retain the catheter.

Figure 2A:
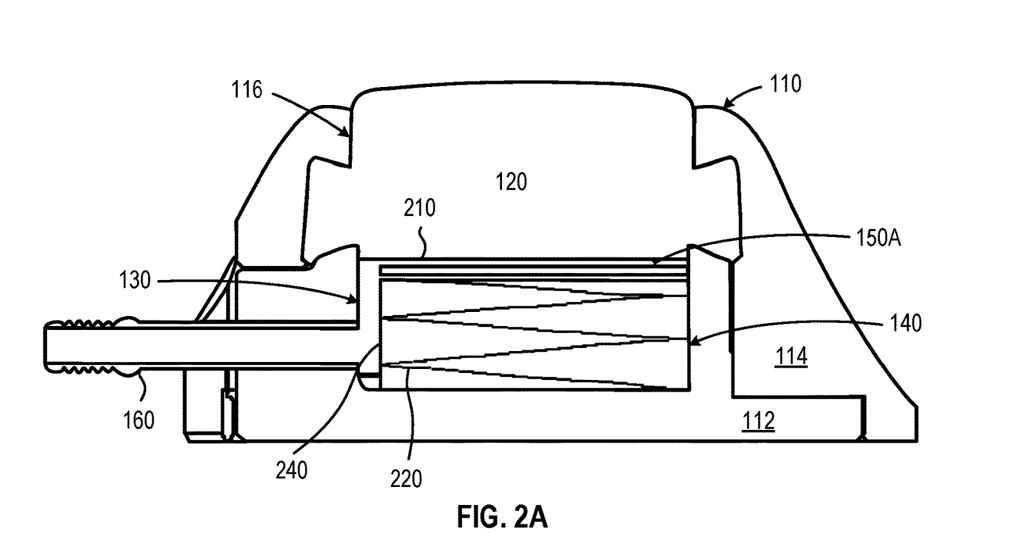
FIG. 2A depicts an illustrative variable volume infusion port with the displaceable member disposed in the first position and in which the displaceable member includes a rigid member and a biasing device, in accordance with at least one embodiment described herein.
Figure 2B:
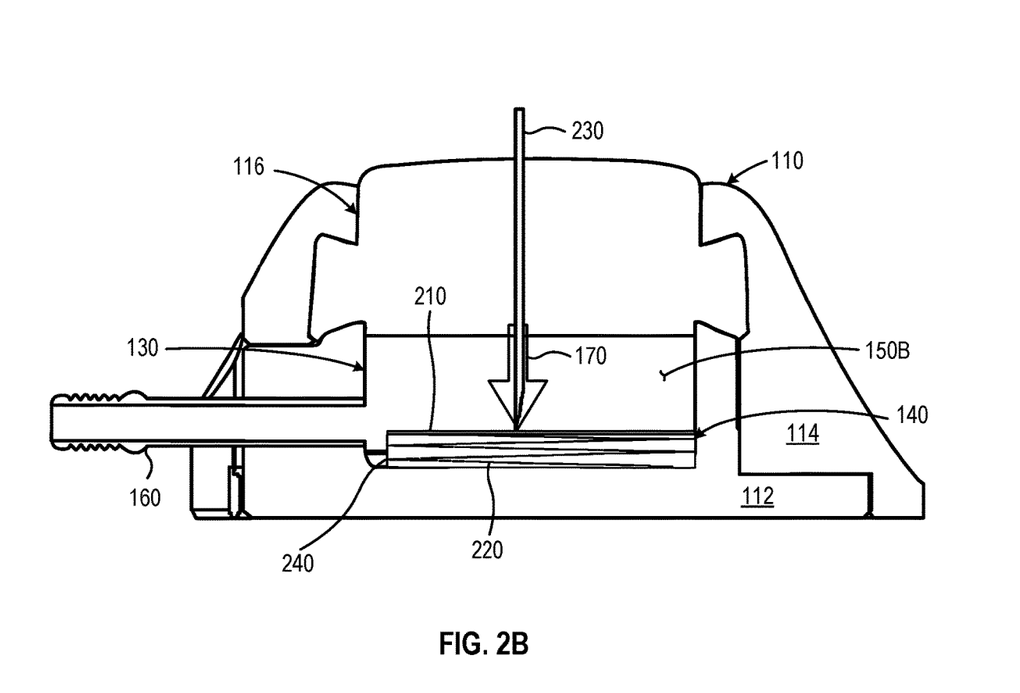
FIG. 2B depicts the illustrative variable volume infusion port in FIG. 2A with an injection device applying a force to the displaceable member to dispose the rigid member in the second position to provide a second fluid volume in the reservoir, in accordance with at least one embodiment described herein.

FIG. 2A depicts an illustrative variable volume infusion port 200 with the displaceable member 140 disposed in the first position and in which the displaceable member 140 includes a rigid member 210 and a biasing device 220, in accordance with at least one embodiment described herein. FIG. 2B depicts the illustrative variable volume infusion port 200 with the displaceable member 140 disposed in the second position, in accordance with at least one embodiment described herein. In one or more embodiments, the displaceable member 140 may include a rigid member 210 that seals against at least a portion of the inner surface of the reservoir 130 and a biasing device 220 that biases the rigid member 210 to the first position proximate the septum 120. An external membrane 240 is disposed about the periphery of the displaceable member 140 to reduce or prevent fluid flow beneath the rigid member 210. A force 170 applied via an injection device 230 causes a downward movement of the rigid member 210.

The rigid member 210 may be formed from any substantially rigid biocompatible material that includes, but is not limited to: ceramic materials, stainless steel alloys, titanium and titanium containing alloys, and/or polymeric materials (e.g., poly ether ketone, "PEEK"). The rigid member 210 may have the same horizontal cross-sectional profile (e.g., diameter) as the reservoir 130. In embodiments, the rigid member 210 may have a different cross-sectional profile than the reservoir 130. In embodiments, the thickness of the rigid member 210 may vary based upon the hardness of the material selected for fabrication of the rigid member 210. The rigid member 210 may have a thickness of: about 5 millimeters (mm) or less; about 3 mm or less; about 2 mm or less; about 1 mm or less; about 0.5 mm or less; about 0.3 mm or less; or about 0.2 mm or less. In some implementations, the rigid member 210 may contact the lower surface of the septum 120 when the displaceable member 140 is disposed in the first position. In some implementations, the rigid member 210 may be separated by a distance from the lower surface of the septum 120 when the displaceable member 140 is disposed in the second position.

The biasing device 220 exerts a force on the rigid member 210 that positions the rigid member 210 in the first position in the absence of the externally applied force 170. As depicted in FIGS. 2A and 2B, the biasing device 220 may include one or more springs or similar force producing devices and/or systems. The biasing device 220 may be fabricated using one or more biocompatible materials, such as stainless steel alloys, titanium, or titanium-containing alloys. Although depicted as a single helical spring in FIGS. 2A and 2B, the biasing device 220 may include any number of helical springs distributed evenly or unevenly beneath the rigid member. The biasing device 220 may be operably coupled or otherwise affixed to the rigid member 210. The biasing device 220 may be operably coupled or otherwise affixed to one or more surfaces forming the reservoir 130, such as the base or walls forming the reservoir 130. In embodiments, the biasing device 220 may have a spring rate of: about 0.5 Newtons per millimeter (N/mm) or less; about 1 N/mm or less; about 1.5 N/mm or less; about 2 N/mm or less; about 3 N/mm or less; about 5 N/mm or less; or about 10 N/mm or less. Although depicted as a helical spring in FIGS. 2A and 2B, the biasing device 220 may include any type, number, and/or combination of springs including, but not limited to: helical springs, conical springs; volute springs, coil springs; and similar. In embodiments, the biasing device 220 may include one or more closed end helical springs; one or more ground end helical springs; one or more conical washers; one or more double closed end helical springs; or one or more open end helical springs.

The injection device 230 may include any type and/or combination of devices capable of penetrating the septum 120, displacing the rigid member 210, and delivering a fluid to reservoir 130. Example injection devices 230 include, but are not limited to: an I.P. needle, a Huber needle, or a needle with a deflective, non-coring tip.

In embodiments an external membrane 240 may be disposed about the biasing member 220. The external membrane 240 prevents fluid in the reservoir 130 from flowing beneath the rigid member 210. The external membrane 240 may be formed from any biocompatible material. In embodiments, the external membrane 240 may be formed from a biocompatible elastomeric material.

Figure 3A:
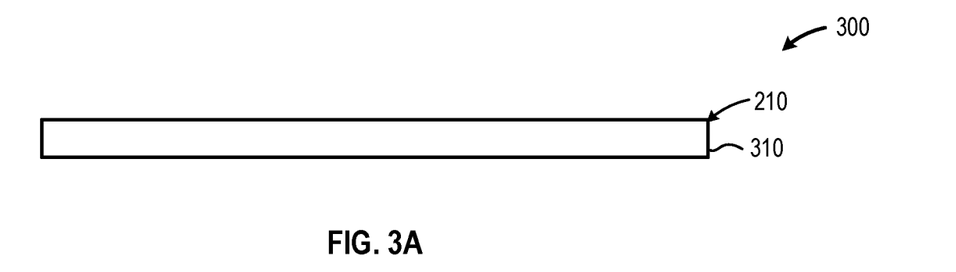
FIG. 3A is a cross-sectional elevation of an illustrative single layer rigid member that forms a portion of the displaceable member, in accordance with at least one embodiment described herein.

FIG. 3A is a cross-sectional elevation of an illustrative single layer rigid member 300A that forms a portion of the displaceable member 140, in accordance with at least one embodiment described herein. As depicted in FIG. 3A, in some embodiments, the displaceable member 140 may include a single layer rigid member 310. The single layer rigid member 310 may be fabricated using any biocompatible material including but not limited to one or more metals, one or more polymers, or one or more ceramics.

Figure 3B:
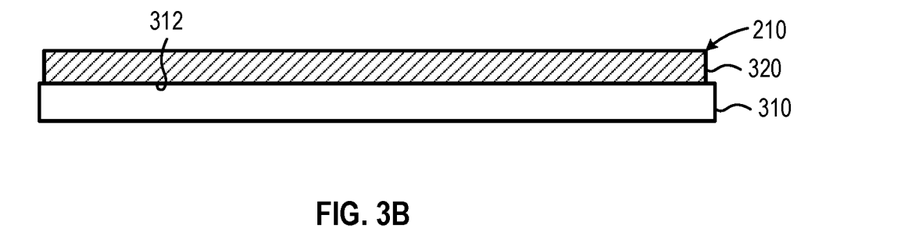
FIG. 3B is a cross-sectional elevation of an illustrative dual-layer rigid member that includes the illustrative single layer rigid member depicted in FIG. 3A with an additional second layer disposed across at least a portion of an upper surface of the single layer rigid member, in accordance with at least one embodiment described herein.

FIG. 3B is a cross-sectional elevation of an illustrative dual-layer rigid member 300B that includes the illustrative single layer rigid member 300A depicted in FIG. 3A with an additional second layer 320 disposed across at least a portion of an upper surface 312 of the single layer rigid member 310. Since the injection device 230 strikes the rigid member 210 upon insertion, the likelihood of damage to the injection device may be mitigated by coating the single layer rigid member 310 with a second layer 320 that includes a softer material less likely inflict damage on the tip of the injection device 230. As depicted in FIG. 3B, a second layer 320 that includes a softer or more resilient material may be disposed on, about, or across at least a portion of the upper surface 312 of the single layer rigid member 310. In embodiments, the second layer 320 may include one or more biocompatible polymers, such as polyether ether ketone (PEEK) and/or silicone. In embodiments, the second layer 320 may have a thickness of: about 1 mm or less; about 0.5 mm or less; about 0.3 mm or less; or about 0.2 mm or less.

Figure 3C:
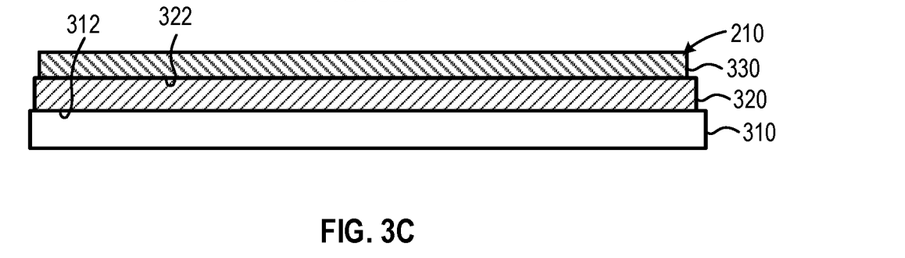
FIG. 3C is a cross-sectional elevation of an illustrative triple-layer rigid member that includes the illustrative dual-layer rigid member depicted in FIG. 3B with an additional third layer disposed across at least a portion of an upper surface of the second layer, in accordance with at least one embodiment described herein.

FIG. 3C is a cross-sectional elevation of an illustrative triple-layer rigid member 300C that includes the illustrative dual-layer rigid member 300B depicted in FIG. 3B with an additional third layer 330 disposed across at least a portion of an upper surface 322 of the second layer 320. As depicted in FIG. 3C, a third layer 330 that includes a softer or more resilient material may be disposed on, about, or across at least a portion of the upper surface 322 of the second layer 320. In embodiments, the third layer 330 may include one or more biocompatible polymers, such as polyether ether ketone (PEEK) and/or silicone. In embodiments, the third layer 330 may have a thickness of: about 1 mm or less; about 0.5 mm or less; about 0.3 mm or less; or about 0.2 mm or less.

Figure 4:
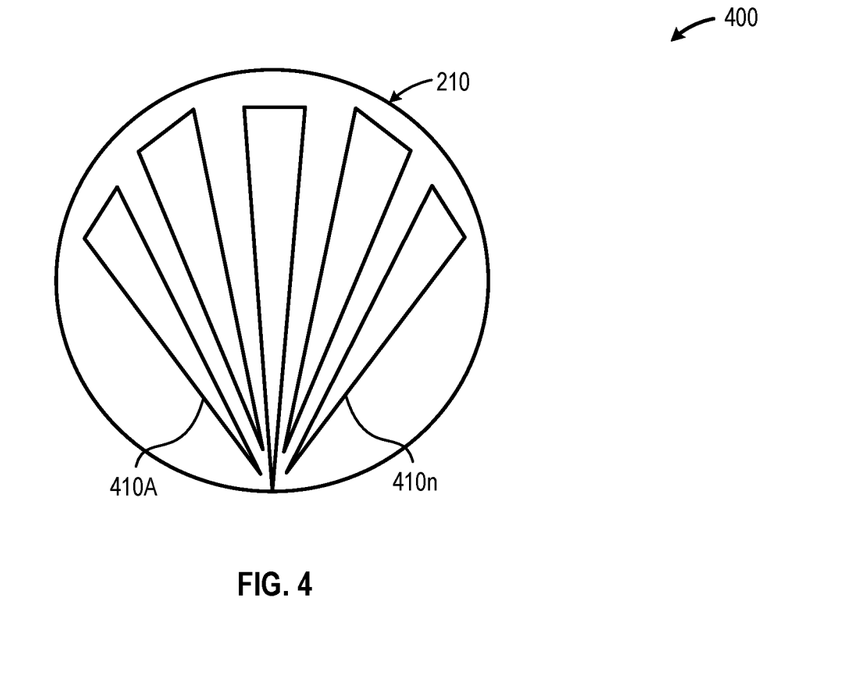
FIG. 4 is a plan view of an illustrative rigid member that includes one or more surface features to promote fluid flow toward the stem, in accordance with at least one embodiment described herein.

FIG. 4 is a plan view of an illustrative rigid member 210 that includes one or more surface features 410A-410n (collectively, "surface features 410") to promote fluid flow toward the stem 160, in accordance with at least one embodiment described herein. The one or more surface features 410 may be formed, deposited, or otherwise disposed in, on, across, or about at least a portion of the upper surface of the rigid member 210. In embodiments, the one or more surface features 410 may project from the upper surface of the rigid member 210. In other embodiments, the one or more surface features 410 may be embedded or recessed in the upper surface of the rigid member 210. The one or more surface features 410 may be formed integral with the rigid member 210. The one or more surface features 410 may be affixed, attached, or otherwise operably coupled to the upper surface of the rigid member 210. The one or more surface features 410 may include but are not limited to any number and/or combination of grooves, ridges, prominences, and/or similar devices intended to assist or promote fluid flow across the upper surface of the rigid member 210 towards the stem 160.

Figure 5A:
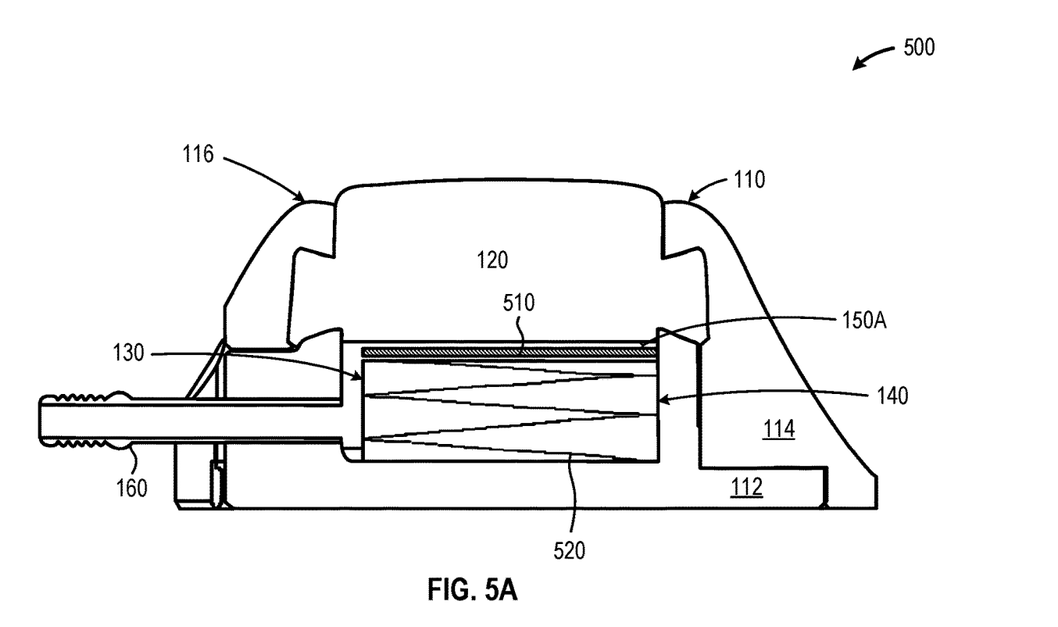
FIG. 5A depicts an illustrative variable volume infusion port that includes a displaceable member having a flexible member and a biasing device that positions the displaceable member in the first position to provide a first fluid volume in the reservoir, in accordance with at least one embodiment described herein.
Figure 5B:
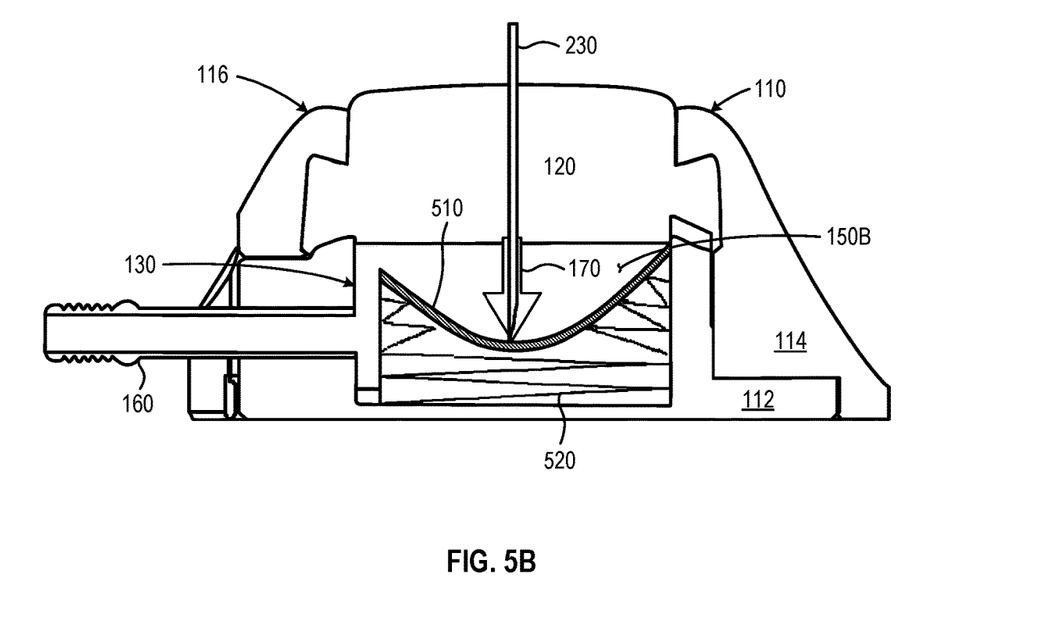
FIG. 5B depicts the illustrative variable volume infusion port in FIG. 5A with an injection device applying a force to the displaceable member to dispose the flexible member in the second position to provide a second fluid volume in the reservoir, in accordance with at least one embodiment described herein.

FIG. 5A depicts an illustrative variable volume infusion port 500 that includes a flexible member 510 and a biasing device 520 forming a displaceable member 140 disposed in the first position to provide a first fluid volume 150A in the reservoir 130, in accordance with at least one embodiment described herein. FIG. 5B depicts the illustrative variable volume infusion port 500 with a force 170 applied to the displaceable member 140 to dispose the flexible member 510 in the second position to provide a second fluid volume 150B in the reservoir 130, in accordance with at least one embodiment described herein. In one or more embodiments, the displaceable member 140 may be formed from a flexible member 510 that seals against at least a portion of the inner surface of the reservoir 130 that is variably and continuously positionable between a first position that provides the first fluid volume 150A in the reservoir 130 and a second position that provides the second fluid volume 150B in the reservoir 130.

As depicted in FIGS. 5A and 5B, in some embodiments, one or more biasing devices 520, such as helical springs, may position the flexible member 510 in the first position proximate the lower surface of the septum 120 in the absence of an externally applied force 170. In one or more constructs, the biasing device 520 may include one or more springs or similar force producing devices and/or systems fabricated using one or more biocompatible materials, such as stainless-steel alloys, titanium, or titanium-containing alloys. Although only a single helical spring is depicted in FIGS. 5A and 5B, the biasing device 520 may include any number of springs or similar biasing elements distributed in an even or uneven pattern beneath the flexible member 510. Although not depicted in FIGS. 5A and 5B, in other constructs, the flexible member 510 and the biasing device 520 may include a unitary, compressible, body fabricated at least in part using a biocompatible, impervious, elastomeric foam (e.g., polyurethane foam) or similar compressible, biocompatible material. In yet other constructs, the biasing device 520 may include a composite structure that includes one or more springs in combination with a biocompatible elastomeric foam. Regardless of the biasing member construct, an external force 170 applied via the injection device 230 causes a downward displacement of at least a portion of the flexible member 510 to the second position to provide the second fluid volume 150B in the reservoir 130.

The flexible member 510 may be formed from any number and/or combination of currently available and/or future developed flexible biocompatible materials. In embodiments, the flexible member 510 may include a multi-layer structure that includes a flexible material, such as KEVLAR®, that is resistant to puncture, tearing, or other physical/mechanical damage caused by the sharp tip of the injection device 230. In embodiments, the flexible member 510 may include a structure having components that allow for movement of the surface contacted by the injection device 230, such as a plurality of nested cylinders. The flexible member 510 may have the same horizontal cross-sectional profile (e.g., diameter) as the reservoir 130. In embodiments, the flexible member 510 may have a different cross-sectional profile than the reservoir 130. In some implementations, at least a portion of the flexible member 510 may contact at least a portion of the lower surface of the septum 120 when in the first position. In the second position, at least a portion of the flexible member 510 may be displaced a distance from at least a portion of the lower surface of the septum 120.

The biasing device 520 exerts a force on the flexible member 510 that positions the upper surface of the flexible member 510 in the first position in the absence of an external force 170. In embodiments, at least a portion of the biasing device 520 may be unitary with, operably coupled, or otherwise affixed to at least a portion of the flexible member 510. In embodiments, at least a portion of the biasing device 520 may be operably coupled or otherwise affixed to all or a portion of the one or more interior surfaces of the reservoir 130, such as the base or walls forming the reservoir 130.

Figure 6A:
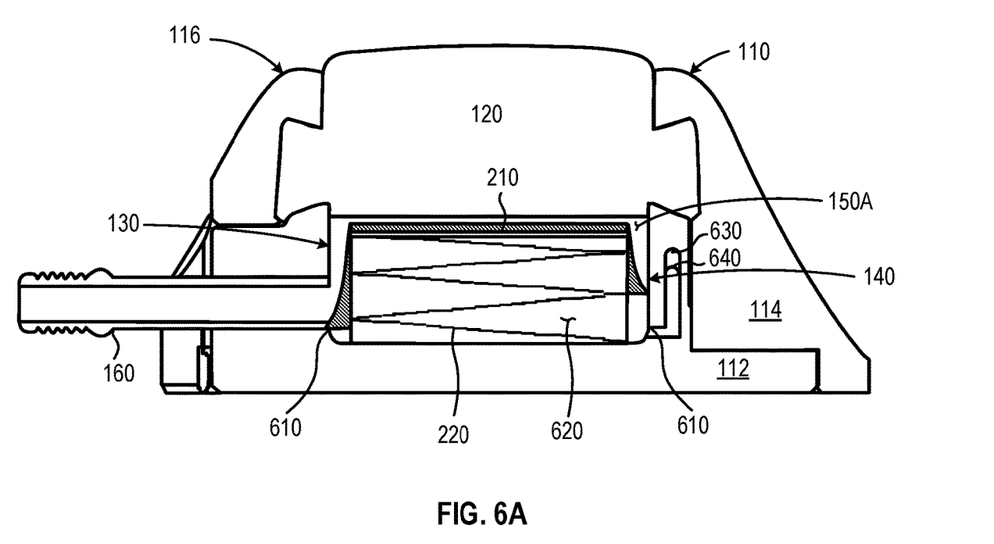
FIG. 6A depicts an illustrative variable volume infusion port that includes a displaceable member having a rigid member and a flexible membrane disposed between the rigid member and the interior surface of the reservoir to provide a fluidly isolated volume beneath the rigid member, in accordance with at least one embodiment described herein.
Figure 6B:
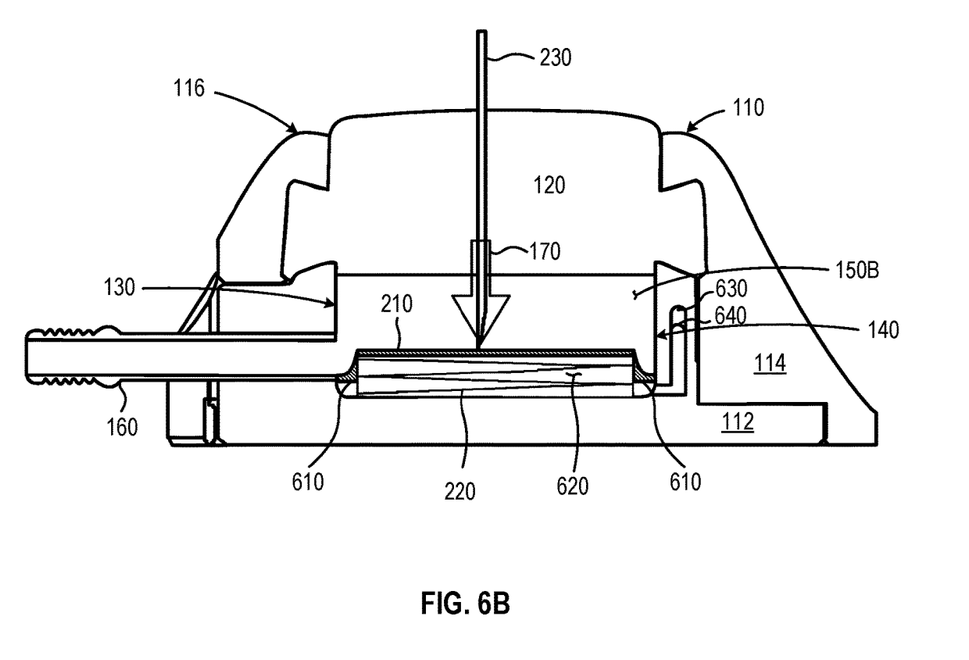
FIG. 6B depicts the illustrative variable volume infusion port of FIG. 6A with an injection device applying a force to the displaceable member to dispose the rigid member in the second position to provide a second fluid volume in the reservoir, in accordance with at least one embodiment described herein.

FIG. 6A depicts an illustrative variable volume infusion port 600 that includes a displaceable member 140 having a rigid member 210 and a flexible membrane 610 disposed between the rigid member 210 and the interior surface of the reservoir 130 to provide a fluidly isolated volume beneath the rigid member 210, in accordance with at least one embodiment described herein. FIG. 6B depicts the illustrative variable volume infusion port 600 with a force 170 applied to the displaceable member 140 to dispose the rigid member 210 in the second position to provide a second fluid volume 150B in the reservoir 130, in accordance with at least one embodiment described herein. In embodiments, the flexible membrane 610 may be coupled to or formed integral with at least a portion of the perimeter of the rigid member 210. In embodiments, the flexible membrane 610 may be coupled to at least a portion of the interior surfaces forming the reservoir 130. The volume 620 beneath the rigid member 210 and membrane 610 is fluidly isolated from the volume (i.e., the first fluid volume 150A and the second fluid volume 150B) above the rigid member 210 and the flexible membrane 610.

In embodiments, the volume 620 may be filled with one or more compressible substances or materials, such as a compressible gas. In other embodiments, the volume 620 may be filled with one or more biocompatible sterile fluids, such as a sterile saline solution. When the volume 620 is filled with a fluid, an overflow chamber 630 formed in the port body 112 may be fluidly coupled to the volume 620 to receive the fluid displaced as the rigid member is moved from the first position to the second position by the application of the external force 170. In such embodiments, a flexible membrane 640 may be disposed in the overflow chamber 630 to return the fluid to the volume 620 in the absence of applied force 170 to the rigid member 210.

The flexible membrane 610 may include any number and/or combination of currently available and/or future developed biocompatible materials capable of providing a flexible, elastomeric seal between at least a portion of the perimeter of the rigid member 210 and at least a portion of an interior surface of the fluid reservoir 130. In embodiments, rigid member 210 may include an elastomeric layer disposed on, about or across at least a portion of the surface of the rigid member 210 and extending outward from the rigid member 210 to form at least a portion of the flexible membrane 610.

As used in this application and in the claims, a list of items joined by the term "and/or" can mean any combination of the listed items. For example, the phrase "A, B and/or C" can mean A; B; C; A and B; A and C; B and C; or A, B and C. As used in this application and in the claims, a list of items joined by the term "at least one of" can mean any combination of the listed terms. For example, the phrases "at least one of A, B or C" can mean A; B; C; A and B; A and C; B and C; or A, B and C.

A variable volume infusion port is provided. The infusion port may include a port body having an internal fluid reservoir, a septum, a stem to fluidly couple to a catheter lumen, and a displaceable member disposed in the internal fluid reservoir. In a first position, the displaceable member is disposed proximate the septum, providing a relatively small fluid volume within the infusion port. Insertion of an injection device through the septum causes the displaceable member to move to a second location distal from the septum, providing a relatively large fluid volume within the infusion port for the duration the injection device remains in the infusion port. The displaceable member may include a rigid member operably coupled to a biasing element or a flexible member coupled to a biasing element.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A variable volume infusion port, comprising:
    a hollow body forming a reservoir, the hollow body including a base and an open top;
    a septum disposed across at least a portion of the open top;
    a hollow stem in fluid communication with the reservoir, the hollow stem projecting at least partially from the hollow body; and
    a displaceable rigid member disposed in the reservoir to provide a variable volume reservoir;
    the displaceable rigid member biased, in an absence of an insertion of an injection device into the reservoir, to a first position proximate the septum such that a first fluid volume is containable in the reservoir;
    at least a portion of the displaceable rigid member displaceable, by the insertion of the injection device into the reservoir, to a second position distal from the septum such that a second fluid volume is containable in the reservoir that is greater than the first fluid volume;
    the displaceable rigid member having an upper surface and a transversely opposed lower surface, wherein the upper surface includes one or more recessed surface features to promote flow towards the hollow stem;
    the one or more recessed surface features to promote flow towards the hollow stem are unoccupied by the septum when the displaceable rigid member is in the first position; and
    the first fluid volume comprises 15% or less of the second fluid volume.

2. The variable volume infusion port of claim 1 wherein one or more springs bias the rigid member to the first position to provide the first fluid volume and wherein the insertion of the injection device into the reservoir compresses the one or more springs and displaces the rigid member to the second position to provide the second fluid volume.

3. The variable volume infusion port of claim 2 wherein the one or more springs comprise at least one of: one or more helical springs; one or more coil springs; one or more conical springs; or one or more volute springs.

4. The variable volume infusion port of claim 1 wherein the rigid member comprises a laminated rigid member that includes a metallic member and a polymer layer disposed proximate at least a portion of the metallic member.

5. The variable volume infusion port of claim 4 wherein the laminated rigid member further comprises a silicone layer disposed proximate at least a portion of the polymer layer.

6. The variable volume infusion port of claim 1 wherein the variable volume infusion port further comprises a subcutaneous infusion port.

7. A variable volume infusion port, comprising:
    an infusion port having a septum and forming an internal reservoir having a longitudinal axis;
    a displaceable rigid member disposed at least partially within the internal reservoir, transverse to the longitudinal axis, the displaceable rigid member to provide a variable fluid volume in the internal reservoir;
    the displaceable rigid member including an upper surface and a transversely opposed lower surface, wherein the upper surface includes one or more recessed surface features to promote flow towards a hollow stem;
    the displaceable rigid member biased, in an absence of an insertion of an injection device into the internal reservoir, to a first position along the longitudinal axis, the first position to provide a first fluid volume within the internal reservoir;
    wherein the insertion of the injection device into the fluid reservoir displaces at least a portion of the displaceable rigid member to a second position along the longitudinal axis, the second position to provide a second fluid volume within the internal reservoir that is greater than the first volume;

wherein the one or more recessed surface features to promote flow towards the hollow stem are unoccupied by the septum when the displaceable rigid member is in the first position; and wherein the first fluid volume comprises 15% or less of the second fluid volume.

8. The variable volume infusion port of claim 7 wherein one or more springs bias the rigid member to the first position to provide the first fluid volume and wherein the insertion of the injection device into the reservoir compresses the one or more springs and displaces the rigid member to the second position to provide the second fluid volume.

9. The variable volume infusion port of claim 8 wherein the one or more springs comprise at least one of: one or more helical springs; one or more coil springs; one or more conical springs; or one or more volute springs.

10. The variable volume infusion port of claim 7 wherein the rigid member comprises a laminated rigid member that includes a metallic member and a polymer layer disposed proximate at least a portion of the metallic member.

11. The variable volume infusion port of claim 10 wherein the laminated rigid member further comprises a silicone layer disposed proximate at least a portion of the polymer layer.

12. The variable volume infusion port of claim 7 wherein the variable volume infusion port further comprises a subcutaneous infusion port.

13. A variable volume infusion port, comprising:
an infusion port having a septum and forming an internal reservoir having a longitudinal axis;
a displaceable rigid member disposed at least partially within the internal reservoir, the displaceable rigid member displaceable along the longitudinal axis to provide a variable fluid volume in the internal reservoir;
the displaceable rigid member biased to a first position along the longitudinal axis, the first position to provide a first fluid volume within the internal reservoir;
the displaceable rigid member displaceable, by insertion of an injection device into the internal reservoir, to a second position along the longitudinal axis, the second position to provide a second fluid volume within the internal reservoir greater than the first volume;
the displaceable rigid member including an upper surface and a transversely opposed lower surface, wherein the upper surface includes one or more recessed surface features to promote flow towards a hollow stem which provides an outlet from the internal reservoir;
wherein the one or more recessed surface features to promote flow towards the hollow stem are unoccupied by the septum when the displaceable rigid member is in the first position; and
wherein the displaceable rigid member is biased exclusively towards the septum.

14. The variable volume infusion port of claim 13 wherein one or more springs bias the rigid member to the first position to provide the first fluid volume and wherein the insertion of the injection device into the reservoir compresses the one or more springs and displaces the rigid member to the second position to provide the second fluid volume.

15. The variable volume infusion port of claim 14 wherein the one or more springs comprise at least one of: one or more helical springs; one or more coil springs; one or more conical springs; or one or more volute springs.

16. The variable volume infusion port of claim 13 wherein the rigid member comprises a laminated rigid member that includes a metallic member and a polymer layer disposed proximate at least a portion of the metallic member.

17. The variable volume infusion port of claim 16 wherein the laminated rigid member further comprises a silicone layer disposed proximate at least a portion of the polymer layer.

18. The variable volume infusion port of claim 13 wherein the variable volume infusion port further comprises a subcutaneous infusion port.

19. The variable volume infusion port of claim 13 wherein the first fluid volume comprises 15% or less of the second fluid volume.

20. The variable volume infusion port of claim 13 wherein the internal reservoir has an internal reservoir volume;
the first fluid volume is 40% or less of the internal reservoir volume; and
the second fluid volume is 50% or more of the internal reservoir volume.

* * * * *